United States Patent [19]

Shirota

[11] 4,348,182

[45] Sep. 7, 1982

[54] REINFORCEMENT WIRE FOR MATERIAL FOR THE IMPRESSION OF DECAYED TOOTH

[75] Inventor: Kazunari Shirota, Tokyo, Japan

[73] Assignee: Shirota Denki Kozai Kabushiki-Kaisha, Tokyo, Japan

[21] Appl. No.: 221,562

[22] Filed: Dec. 31, 1980

[51] Int. Cl.³ .............................................. A61C 9/00
[52] U.S. Cl. ................................... 433/214; 433/221; 433/225
[58] Field of Search ............... 433/214, 215, 218, 219, 433/220, 221, 222, 223, 224, 225, 226, 102

[56] References Cited

U.S. PATENT DOCUMENTS

| 674,419 | 5/1901 | Kinsman | 433/224 |
| 1,168,052 | 1/1916 | Bolls | 433/102 |
| 1,211,244 | 1/1917 | Schroeder et al. | 433/226 |
| 2,094,308 | 9/1937 | Snell | 433/214 |
| 4,253,835 | 3/1981 | Ware | 433/220 |

FOREIGN PATENT DOCUMENTS

| 117906 | 1/1947 | Sweden | 433/220 |
| 549473 | 11/1942 | United Kingdom | 433/214 |

Primary Examiner—Gene Mancene
Assistant Examiner—John J. Wilson
Attorney, Agent, or Firm—Shlesinger, Fitzsimmons & Shlesinger

[57] ABSTRACT

A stainless steel wire bonded with a number of short filaments or staple fibers which are electrostatically bonded to the wire, said filaments being engaged in a jerry material which is applied over a decayed tooth for taking an impression thereof, when the wire is embeded into said jerry material for the reinforcement thereof.

1 Claim, 2 Drawing Figures

REINFORCEMENT WIRE FOR MATERIAL FOR THE IMPRESSION OF DECAYED TOOTH

This invention relates to a reinforcement wire for a jerry material for the impression of a decayed tooth, which impression is utilized for making an artificial tooth which is to be joined to the decayed tooth.

Utility of the reinforcement wire is more fully described in the following.

Figure 1:
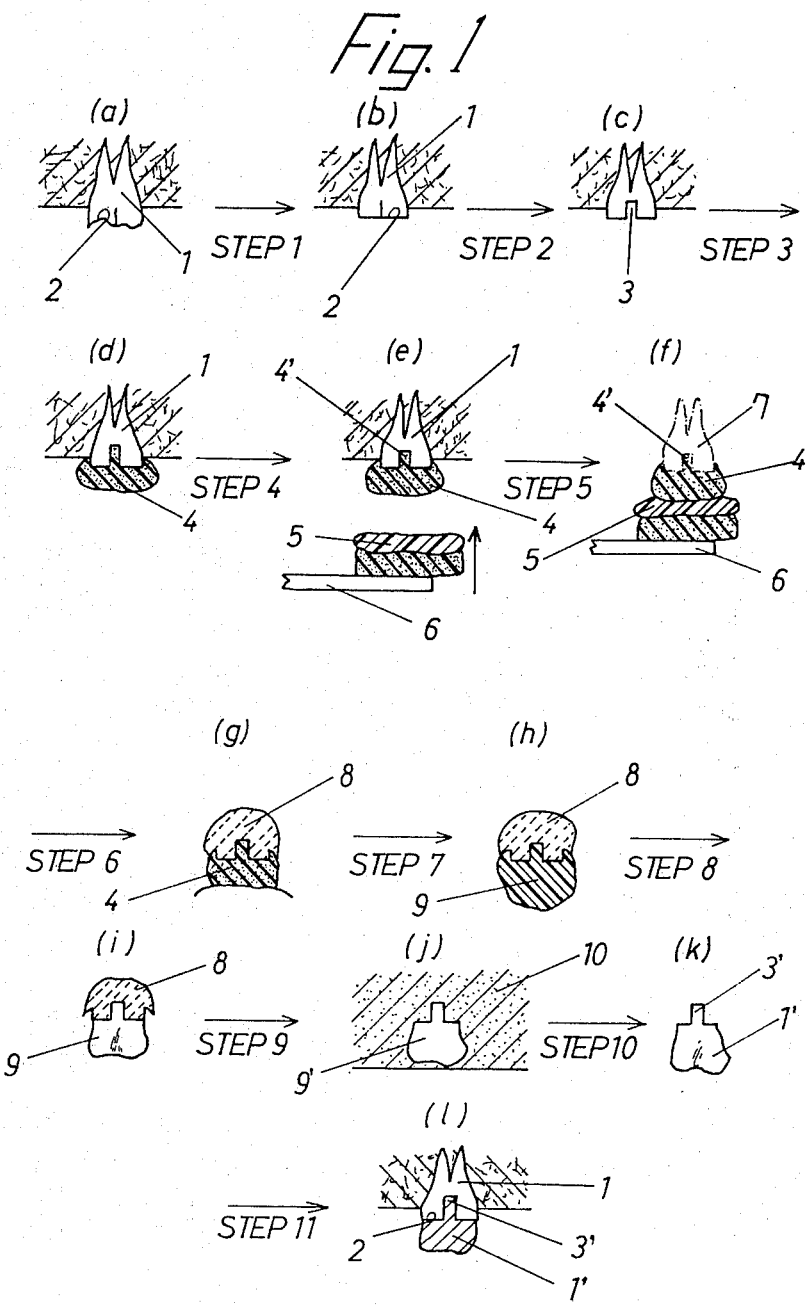
Figure 2:
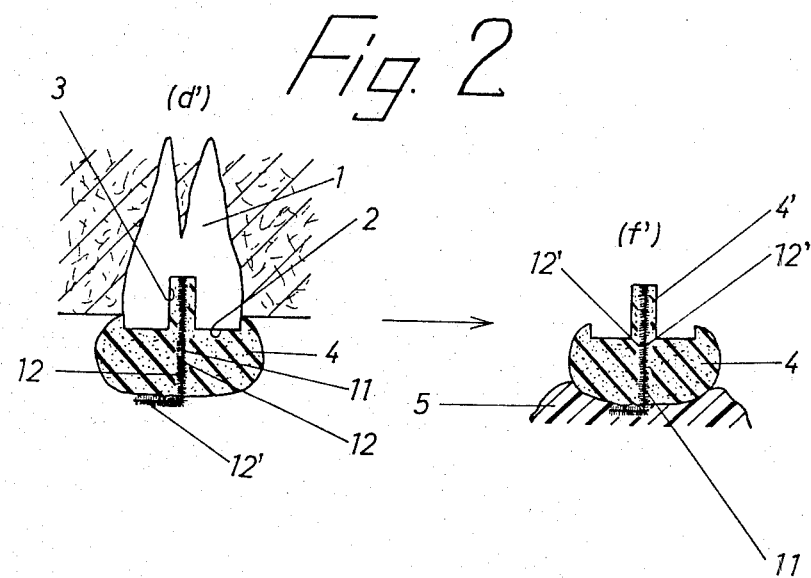

In the accompanying drawings;

FIG. 1 schematically illustrates eleven steps for preparing an artificial tooth and joining it to a decayed tooth, and FIG. 2 shows the reinforcement wires of this invention, which are utilized in the aforementioned steps.

Crowning a decayed tooth with an artificial tooth is made as explained hereinunder with reference to FIG. 1.

The remnant 1 of a decayed tooth is made flat at its outer surface 2 by grinding it (Step 1); a post hole 3 is provided to the remnant by drilling it centrally (Step 2); the outer surface 2 is covered by a jerry material 4 such as warmed and softened agar-agar, plastic silicone resin and so on, and consequently the post hole 3 is filled up with the material for producing impressions of the surface and post hole (Step 3). When the material 4 is solidified, alginate, a resinous material 5 which is put on a tray 6 and kept plastic, is gently pressed over the solidified agar-agar (Step 4). When the alginate is hardened over the agar-agar, the tray is removed from the mouth thus withdrawing the agar-agar which now has formed on its upper surface an impression 7. This impression includes the flat outer surface 2 of the tooth remnant 1 and a projected impression 4' of the post hole 3 (Step 5). Over the agar-agar impression 4, there is now placed moist plaster 8, the configuration of which is correspondent, when set, to that of the outer surface 2 and the post hole 3 of the tooth remnant 1 (of FIG. 1(c)) (Step 6). The set plaster 8 is then removed from the agar-agar impression 4, and wax 9 is set on the plaster mold 8 (Step 7). Wax 9 is then shaped so as to have a configuration of an artificial tooth which is to be joined to the remnant tooth 1 (Step 8); and this wax artificial tooth 9 is removed from the plaster 8, and is embedded in a sand mold 10 and burnt so that a mold cavity 9' having the configuration of the desired artificial tooth is made in the mold (Step 9). The cavity 9' is then filled with metallic or ceramic materials to produce a metallic or ceramic artificial tooth 1' having a post 3' (Step 10); and the artificial tooth 1' is joined to the tooth remnant 1 by insertedly fitting the post 3' into the hole 3 and cementing them and the surface 2.

Among the above steps 1 to 11 which all require delicate operations, Step 5 which involves the removal or solidified agar-agar 4 from the tooth 1, or more particularly the removal of a slender projection 4' of said agar-agar 4, configuration of which matches the narrow hole 3 of tooth 1, and Step 6 which involves setting plaster over the delicate agar-agar 4 are most difficult to successfully complete them without deforming, distorting, or tearing off the projection 4'. For this reason, in this invention, a reinforcement pin 11 covered by a number of short filaments or staple fibers 12 which project outwardly from the pin and radially to the axis thereof, is employed in a step following the Step 3 of FIG. 1. In the Step 6 of FIG. 1, too, the pin 11 works effectively to prevent the distortion of the projection 4'.

In FIG. 2, illustration (d') is correspondent to FIG. 1(d), and (f') to FIG. 1(f). When the tooth 1 is covered and filled up by agar-agar 4 at its outer surface 2 and post hole 3, as shown in FIG. 1(d), the pin 11 having a length sufficient enough to reach the bottom of post hole 3 of tooth 1 at its one end and to extend outwardly from the agar-agar 4 at its another end, which forms a portion 12' bent at a right angle, is gently inserted into the agar-agar. As shown in FIG. 2(d'), the pin 11 which lies centrally and extends longitudinally within the agar-agar and firmly engages with the agar-agar by means of the fibers 12, reinforces said agar-agar particularly its projection 4'. Hence, the projection 4' is scarcely distorted or torn off when Step 5 is performed. Also, as shown in FIG. 2(f'), the projection 4' thus reinforced by the pin 11 shall not be distored or deformed when plaster is applied thereover as illustrated in FIG. 1(g). It shall be noted that the pin 11 can get set or secured well within the agar-agar on account of filaments or fibers 12 which extend radially outwardly from the pin.

The pin 11 of this invention is made as follows.

A stainless steel wire of about 0.2 to 0.3 mm in diameter is washed and degreased by carbon tetrachloride. It is then coated by a diluted solution of phosphoric acid for forming its film thereupon which works to improve the attachment of adhesives thereto. The wire is thereafter coated with an epoxy resin. The resin thus applied over the wire surface is hardened by amine, and is covered by polyamide so that the outer surface of wire becomes adhesive.

In a chamber, said wire is charged under 40,000 V so that it is charged positive, while short filaments of nylon of 1.5 denier and of 0.3–0.5 mm in length are charged negative. The wire thus has bonded to its outer surface about 25,000 filaments/cm$^2$ which thickness is about 90$\mu$, and approximately the outer 50$\mu$ of which consist of those filaments which project radially outwardly from the wire. After keeping the wire for 12 hours as it is processed, it is subjected to an air spray once, and then brushed by a vacuum.

What is claimed is:

1. A reinforcement for use with a jerry material such as agar agar, silicone resin and so on, which material is pressed over a decayed tooth, which is made flat at its outer surface, and which projects into a hole provided in the tooth, and is solidified for producing an impression of said tooth for joining thereto an artificial tooth by means of said hole and a corresponding post provided on the artificial tooth; said reinforcement comprising a wire body piece and a plurality of short filaments or staple fibers fixed to said piece and projecting radially outwardly therefrom, said filaments or fibers being engaged in the surrounding jerry material when the wire piece is embedded in the jerry material, particularly in the projecting portion thereof which mates with the hole of the decayed tooth, and wherein the wire body piece comprises a stainless steel wire, and the filaments and fibers are made from nylon or rayon fibers which are electrostatic-bonded to the wire.

* * * * *